Figure 1:
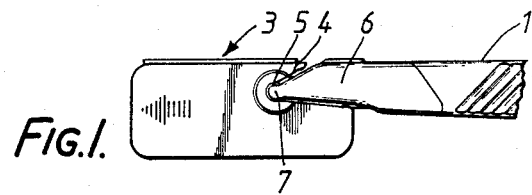

United States Patent [19]
Chase et al.

[11] Patent Number: 4,825,545
[45] Date of Patent: May 2, 1989

[54] KNIVES WITH MOLDED PROTECTIVE COVER AND HANDLE

[75] Inventors: Anthony J. Chase, Camberley; John E. Payne, Reading, both of England

[73] Assignee: Sabre International Products Limited, Berkshire, England

[21] Appl. No.: 125,500
[22] PCT Filed: Mar. 17, 1987
[86] PCT No.: PCT/GB87/00186
 § 371 Date: Nov. 18, 1987
 § 102(e) Date: Nov. 18, 1987
[87] PCT Pub. No.: WO87/05485
 PCT Pub. Date: Sep. 24, 1987

[30] Foreign Application Priority Data
 Mar. 18, 1986 [GB] United Kingdom ............... 8606601

[51] Int. Cl.⁴ ................... B26B 29/00; A61F 17/32
[52] U.S. Cl. .................................. 30/153; 128/305; 30/284; 30/286
[58] Field of Search ............. 30/153, 151, 284, 329, 30/285, 286; 128/305

[56] References Cited
U.S. PATENT DOCUMENTS
1,332,254  3/1920  Hart .
3,748,736  7/1973  Eisen .
3,793,726  2/1974  Schrank ........................ 30/151

FOREIGN PATENT DOCUMENTS
8535978  3/1986  Fed. Rep. of Germany .
1501959  11/1967  France .
2487188  1/1982  France .

Primary Examiner—Frank T. Yost
Assistant Examiner—Willmon Fridie, Jr.
Attorney, Agent, or Firm—Watson, Cole, Grindle & Watson

[57] ABSTRACT

A knife, such as a surgical scalpel or a handymans knife has a protective blade cover (3) moulded integrally with the handle of the knife. The end portion of the knife and the cover are both formed in mating halves about a common fold line and the knife blade is secured by folding the halves over each other to trap the blade and securing, as by welding, The cover has a part-circular recess (5) to receive a part-circular tip (7) at the end of the handle. The knife and cover are connected together only by a frangible web between the recess (5) and the tip (7). When the web is ruptured for first removal of the cover, the tip (7) has snap-fitting engagement in the recess (5) to permit replacement and retention of the cover.

5 Claims, 2 Drawing Sheets

KNIVES WITH MOLDED PROTECTIVE COVER AND HANDLE

This invention relates to knives having removable protective covers for their cutting edges. The invention is particularly applicable to the design and manufacture of disposable surgical scalpels, but is also applicable to other knives, such as for model making or other domestic uses.

In accordance with a feature of the invention, a knife comprises a plastics moulded handle, to which a knife blade is secured, and a removable protective cover, for at least the cutting edge of the blade, formed integrally with the handle.

In a preferred form of the invention, both an end portion of the handle and the cover are each moulded in two generally co-planar halves connected together along a common fold line, and the halves of the cover are connected frangibly to the halves of the handle part, so that a blade can be located and secured in position by folding over the moulding and securing the respective halves together (as by welding).

Figure 2:
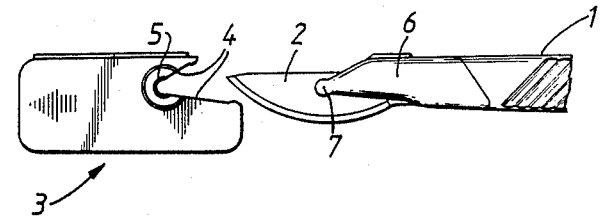
Figure 3:
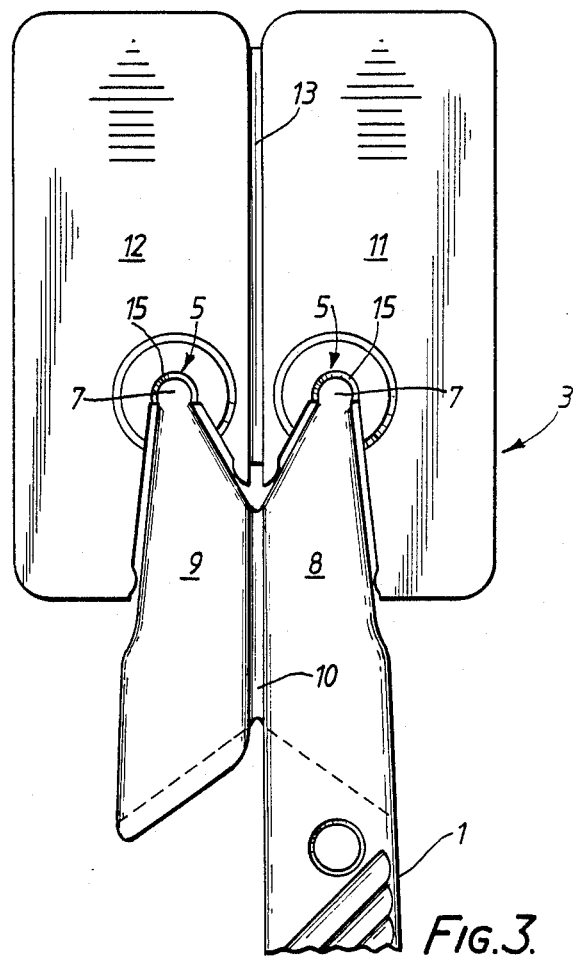
Figure 4:
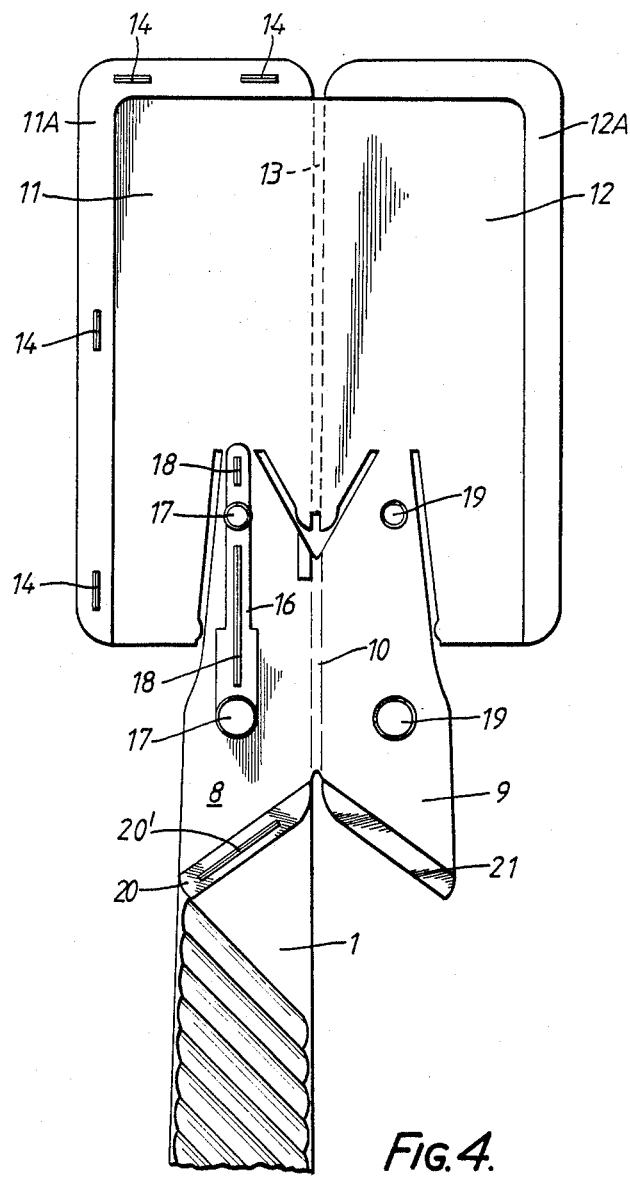

This preferred form of the invention will now be described by way of example, with reference to the accompanying drawings, in which:

FIGS. 1 and 2 show a disposable scalpel with the cover in position to protect the blade, and having been removed, respectively; and FIGS. 3 and 4 are views of the unitary moulding for the handle and cover, as moulded, from opposite sides.

The scalpel shown in FIGS. 1 and 2 comprises a handle 1 having a blade 2 set into one end of the handle, and a removable protective cover 3, which completely envelops the blade as shown in FIG. 1, until removed for use of the scalpel (FIG. 2).

As will be described in detail below, the cover 3 is formed integrally with the handle and is actually closed and formed in the same operation in which the blade is secured in position, thus assuring the integrity of the blade edge from that time on, until deliberately removed when the scalpel is to be used.

The side walls of the cover are formed with matching notches 4 each having the form of an acute angle with a circular recess 5 at the apex, the recess having an arcuate extent in excess of 180°. The adjacent end portion 6 of the handle is shaped, on either side of the blade, to fit easily into the notch 4 and terminates in a part-circular tip 7 located in the recess 5. The cover 3, which is otherwise separate from the handle, is removed by pulling it longitudinally away from the handle, the resilience of the material enabling the tips 7 to snap out the corresponding recesses 5.

Although the cover of a disposable surgical scalpel does not strictly need to be replaced, since the scalpel should be used for only one incision, the cover can be snap fitted back into position if desired, e.g. to shield the edge for disposal of the scalpel. For knives intended for repeated use, the interconnecting portions can be dimensioned to be more durable to withstand repeated engagement and disengagement of the parts.

FIGS. 3 and 4 show the plastics parts of the knife on a larger scale, in the form in which they are moulded.

The major part of the handle is solid, of a generally flattened rectangular cross-section, but the end portion of the handle is formed in two generally co-planar halves 8, 9 connected together along a fold line 10. The cover is correspondingly formed in two halves 11, 12 connected to each other along an extension 13 of the fold line 10. The cover halves are connected to the handle halves only by frangible arcuate webs 15 around the tips 7, as seen in FIG. 3, which shows the eventual outer surfaces of the respective halves.

As seen in FIG. 4, the interior surfaces of the cover halves are completely smooth and planar, except for slightly raised boundary wall portions 11A, 12A extending along two sides. These portions have in turn a number of energy director pips 14 for eventual welding of the wall portions together by ultrasonic welding.

The inner surface of the handle half 8 is generally planar, except for raised rib 16 shaped to fit a standard, elongate hole in a scalpel blade. The rib also has two raised circular pips 17 and elongate energy directors 18.

The inner surface of the other half 12 is planar except for two circular recesses 19 destined to receive the pips 17 when the halves are folded over against each other.

At the transition between the solid portion of the handle and the adjacent edge of the half portion 8, there is a chamfered surface 20 having an energy director rib 20'. The corresponding rear edge 21 of the half 9 is also chamfered to mate with the surface 20.

In assembly, a finished blade is positioned over the rib 16, and the half portions 9 and 12 are folded over through 180° about the common fold line 10, 13, and ultrasonically welded to their opposite halves at the locations of the energy directors 14, 18 and 20.

During these operations, the frangible webs 15 are ruptured, so that the cover is retained to the handle by the engagement of the tips 7 in the recesses 5, any residue of the frangible web is readily ruptured by the act of deliberate removal of the cover. The scalpel is now ready for packaging and despatch to its eventual destination.

The main advantages of the scalpel are:

that the handle and cover are formed from a single moulding;

the act of securing the blade to the handle also completes the cover, in situ over the blade;

the blade edge is protected from the time the blade is secured to the handle;

the cover is securely positioned against inadvertent removal;

the blade is firmly secured in the handle and supported from both sides, by virtue of the sandwich construction.

We claim:

1. An integral plastic holder for a knife blade which comprises a first handle portion which has a front end, a rear end, a left side and a right side, said first handle portion including mounting means on its right side near its front end for a knife blade, a second handle portion which is attached to said first handle portion near said front end thereof via a first fold line, said second handle portion having a front end, a rear end, a left side and a right side, a first generally flat cover portion which is attached to the front end of said first handle portion via a first frangible web, and a second generally flat cover portion which is attached to the front end of said second handle portion via a second frangible web and to said first cover portion via a second fold line, said second handle portion and said second cover portion being simultaneously bendable around said first and second fold lines to clamp a knife blade which has been positioned on said mounting means between said first and second handle portions, said first and second cover portions simultaneously covering a front end of said knife blade, said first and second frangible webs being thereafter breakable by a user to disconnect said first and second cover portions from said first and second handle portions to expose the front end of said knife blade.

2. An integral plastic knife blade holder according to claim 1, wherein said front end of said first handle portion includes a first partially circular projection, wherein said first generally flat cover portion includes a partially circular recess in which said first partially circular projection extends, wherein said first frangible web connects said first partially circular projection with said first partially circular recess, wherein said second handle portion includes a second partially circular projection, wherein said second generally flat cover portion includes a partially circular recess in which said second partially circular projection extends, and wherein said second frangible web connects said second partially circular projection with said second partially circular recess.

3. An integral plastic knife blade holder according to claim 2, wherein said partially circular recesses in said first and second generally flat cover portions have arcuate extents of greater than 180° such that, after said first and second frangible webs have been broken, said first and second cover portions are disconnected from said first and second handle portions by snapping said first and second partially circular projections out of said first and second generally circular recesses.

4. An integral plastic knife blade holder according to claim 1, wherein said support means on said first handle portion comprises two spaced apart pips which can extend through an opening in a knife blade, and wherein said second handle portion includes two spaced apart recesses in left side thereof, said two recesses being located so that, when said second handle portion is bent around said first fold line and pressed against said first handle portion, said pips will fit within said recesses.

5. An integral plastic knife blade holder according to claim 4, wherein the right side of said first handle portion is recessed at its front end such that when said second handle portion is bent around said first fold line and pressed against said first handle portion, said second handle portion will fit within said recess.

* * * * *